United States Patent
Kurz et al.

(12)

(10) Patent No.: US 6,436,374 B1
(45) Date of Patent: Aug. 20, 2002

(54) LIGHT-STABLE COSMETIC FORMULATION CONTAINING BUTYLMETHOXYDIBENZOYLMETHANE

(75) Inventors: Thekla Kurz; Dorothee Wille, both of Darmstadt; Sabine Hitzel, Messel, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 09/530,908

(22) PCT Filed: Oct. 31, 1998

(86) PCT No.: PCT/EP98/06902
§ 371 (c)(1),
(2), (4) Date: May 8, 2000

(87) PCT Pub. No.: WO99/24000
PCT Pub. Date: May 20, 1999

(30) Foreign Application Priority Data

Nov. 12, 1997 (DE) .......................... 197 50 030

(51) Int. Cl.$^7$ .......................... A61K 7/42; A61K 7/44; A61K 7/00
(52) U.S. Cl. .......................... 424/59; 424/60; 424/401
(58) Field of Search ............... 424/401, 59, 60

(56) References Cited

U.S. PATENT DOCUMENTS

| | | | | |
|---|---|---|---|---|
| 4,663,157 A | * | 5/1987 | Brock | 424/59 |
| 5,725,844 A | * | 3/1998 | Gers-Barlag et al. | 424/59 |
| 5,788,952 A | * | 8/1998 | Gers-Barlag et al. | 424/59 |
| 5,827,508 A | * | 10/1998 | Tanner et al. | 424/59 |
| 5,866,148 A | * | 2/1999 | Hansenne et al. | 424/401 |
| 5,932,232 A | * | 8/1999 | De Salvert et al. | 424/401 |
| 5,968,484 A | * | 10/1999 | Habeck et al. | 424/59 |
| 5,985,925 A | * | 11/1999 | Josso et al. | 514/557 |
| 6,143,850 A | * | 11/2000 | Keller et al. | 526/304 |
| 6,174,517 B1 | * | 1/2001 | Hansenne et al. | 424/59 |

FOREIGN PATENT DOCUMENTS

| | | |
|---|---|---|
| DE | 4227806 | 2/1993 |
| EP | 0193387 | 9/1986 |
| EP | 0610926 | 8/1994 |
| EP | 0898955 | 3/1999 |
| GB | 2 259 014 A * | 3/1993 |
| JP | 361257915 A * | 11/1986 |
| JP | 408048614 A * | 2/1996 |
| WO | 9801107 | 1/1998 |
| WO | 9813016 | 4/1998 |

* cited by examiner

*Primary Examiner*—Jose' G. Dees
*Assistant Examiner*—Marina Lamm
(74) *Attorney, Agent, or Firm*—Millen, White, Zelano & Branigan, P.C.

(57) ABSTRACT

A cosmetic preparation having butylmethoxydibenzoyhmethane as a protection filter and insoluble inorganic particles which are titanium dioxide particles doped with cerium or iron ions which absorb in the UVA region and are added to improve the photostability of the cosmetic preparation.

10 Claims, No Drawings

LIGHT-STABLE COSMETIC FORMULATION CONTAINING BUTYLMETHOXYDIBENZOYLMETHANE

This application is a 371 of PCT/EP98/06902 filed Oct. 31, 1998.

The present invention relates, inter alia, to the use of insoluble inorganic particles which absorb in the UVA region for improving the photostability of the organic light protection filter butylmethoxydibenzoylmethane in cosmetic formulations.

As is known, the skin is sensitive to solar rays, which can cause ordinary sunburn or an erythema, or also burns of greater or lesser severity.

Solar rays do, however, also have other negative effects: they cause the skin to lose its elasticity and wrinkles to form, and thus lead to premature ageing. In some cases, dermatoses can also be observed. In the extreme case, it results in the appearance of skin cancer in some people.

As is known, the most dangerous part of solar rays is formed by the ultraviolet rays having a wavelength of less than 400 nm. It is also known that, as a result of the presence of the ozone layer in the Earth's atmosphere, which absorbs some of the solar radiation, the lower limit of the ultraviolet rays which reach the Earth's surface is about 280 nm.

The problem with many sunscreen preparations is, however, that many light protection filters are sensitive substances and have low stability towards the ultraviolet rays; they break down at a greater or lesser rate. This results in problems with the shelf life and effectiveness of the corresponding cosmetic formulations. These preparations do not exhibit permanent effectiveness during prolonged solar irradiation, meaning that repeated application to the skin is necessary at regular intervals.

The sun protection filters customarily used today in cosmetics are divided into UVA filters and UVB filters. For both UV regions, there are many tried and tested compounds known from the specialist literature, compounds cited here merely by way of example being hose such as Eusolex® 6300 or Eusolex® 232, dibenzoylmethanes, such as Eusolex® 9020 or Eusolex® 8020, benzophenones and also octyl triazone (Uvinul® T 150).

Butylmethoxydibenzoylmethane (BMDM, Eusolex® 9020) is a UVA filter which is frequently used, but which is severely degraded by UV irradiation. If this substance is processed with other organic UVA filters in a formulation, the stability of the BMDM does not increase.

There is still, therefore, a lack of substances which can be added to the formulations to stabilize the light protection filter BMDM, but which otherwise do not negatively impair the action and the composition of the cosmetic preparations.

It therefore appears desirable to provide cosmetic preparations which are more stable with regard to the light protection filters and which comprise at least the light protection filter butylmethoxydibenzoylmethane and which can absorb predominantly the UVA rays having a wavelength between 320 and 400 nm, which cause the skin to tan, but also to age, favour the onset of an erythematous reaction or heighten this reaction in certain individuals, or can even trigger phototoxic or photoallergic reactions, but which also, if desired, can absorb the UVB rays having a wavelength between 280 and 320 nm, which play a decisive role in the formation of a solar erythema.

Surprisingly, we have now found that the photostability of butylmethoxydibenzoylmethane is increased if insoluble inorganic particles which have good absorption in the UVA region are added.

These substances have the great advantage that they do not display toxic or allergic reactions towards the skin.

The effectiveness of the inorganic UVA filters is to be attributed to the fact that, being insoluble substances, they cannot penetrate the skin, and as a result remain in a layer on the skin. BMDM, being an organic molecule, diffuses into the uppermost layers of the horny skin meaning that from one applied formulation a two-layer system is formed. The lower layer, i.e. the butylmethoxydibenzoylmethane, is therefore reached only by relatively small amounts of energy, resulting in reduced degradation of the organic light protection filter.

This penetration effect can be further enhanced by the use of penetration promoters, such as, for example, dimethyl sulfoxide or diethyltoluamide.

The invention therefore provides for the use of insoluble inorganic particles which absorb in the UVA region for improving the photostability of the light protection filter butylmethoxybenzoylmethane in cosmetic formulations.

These particles include mainly microfine titanium dioxide, which is in the form of the rutile modification, but can also be in the form of anatase, microfine iron oxide, cerium oxide or zinc oxide. The particle size of these particles is in the range from 10 nm to 100 $\mu$m, preferably in the range from 10 nm to 10 $\mu$m.

In a very particularly preferred embodiment of this invention, titanium dioxide microrutile having a particle size of up to 10 $\mu$m is used. This titanium dioxide microrutile is known under the name Eusolex® T-2000 and is available commercially (Merck KGaA, Darmstadt). The microfine titanium dioxide in rutile form has very good UVA absorption and is particularly highly suitable for the photostabilization of BMDM according to the invention.

It is also possible to use insoluble titanium dioxide particles which have been doped, for example, with cerium or iron ions.

The invention also provides a cosmetic preparation comprising the light protection filter butylmethoxydibenzoylmethane, characterized in that, to improve the photostability of this light protection filter, insoluble inorganic particles which have good absorption in the UVA region are added.

The invention further provides a process for improving the photostability of butylmethoxydibenzoylmethane in cosmetic preparations, characterized in that insoluble inorganic UVA filter particles are added.

The content of butylmethoxydibenzoylmethane in the cosmetic preparation according to the invention is preferably from 0.1 to 10% by weight, particularly preferably from 0.5 to 3% by weight.

The content of inorganic particles is from 0.1 to 30% by weight, particularly preferably from 0.5 to 10% by weight.

The light protection filter butylmethoxydibenzoylmethane can be present in the cosmetic formulations according to the invention on its own or in combination with one or more UVA filters from different classes of substance, which can in each case be present in an amount of from 0.01 to 40% by weight, preferably from 0.1 to 10% by weight.

The corresponding microfine pigments are known and can be obtained commercially, e.g. from Merck KGaA, Darmstadt.

They exhibit excellent properties, such as very good skin and mucosa compatibility without toxic, allergenic or sensitizing properties, and no skin penetration.

The substance also has high chemical stability, i.e. does not undergo hydrolysis, photooxidation or oxidation, and has high thermal stability and good perspiration resistance.

Furthermore, this substance is highly compatible and miscible with common cosmetic and pharmaceutical formulation bases.

The invention further provides a process for protecting the skin from solar rays, a cosmetic preparation according to the present invention being applied to the skin.

The formulations according to the invention can also be used for the preventative treatment of inflammations and allergies of the skin, and for preventing certain types of cancer.

In a preferred embodiment of this invention, the cosmetic formulation is in the form of a set of two separate formulations, one formulation of which, which is applied first, comprises butylmethoxydibenzoylmethane, and the second formulation of which, which is applied subsequently, comprises the inorganic particles. This immediately forms the desired two-layer system.

If the cosmetic preparation according to the invention is used to protect the human epidermis against UV rays, it is in various forms customarily used for this type. For example, it can, in particular, be in the form of oily, oily-aqueous, aqueous-alcoholic or oily-alcoholic lotions, emulsions, such as cream or milk (W/O or O/W, where W=water and O=oil), in the form of oily-alcoholic, oily-aqueous or aqueous-alcoholic gels, or as solid sticks or powders, or formulated as a spray or aerosol.

The formulation according to the invention can comprise further cosmetic additives which are customarily used in this type of preparations, such as, for example, thickeners, emollients, moisturizers, surfactants, preservatives, antifoams, perfumes, waxes, lanolin, propellants, dyes and/or pigments which colour the composition itself or the skin, and other ingredients customarily used in cosmetics.

The solubilizing agent can be an oil, wax or other fatty substance, a lower monoalcohol or a lower polyol or mixtures thereof. Particularly preferred monoalcohols or polyols include ethanol, isopropanol, propylene glycol, glycerol and sorbitol.

A preferred embodiment of the invention is an emulsion which is in the form of a protective cream or milk and which, in addition to the organic light protection agents and the inorganic UVA filters, comprises fatty alcohols, fatty acid esters, in particular triglycerides of fatty acids, fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener such as diatomaceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is usually made of the customary propellants, such as alkanes, fluoroalkanes and chlorofluoroalkanes.

If a formulation is formulated as a spray, use is usually made of aqueous-alcoholic solutions.

The cosmetic preparations according to the invention can be prepared using techniques which are well known to the person skilled in the art.

It is assumed that a person skilled in the art will be able to utilize the above description in the widest sense without further explanations. The preferred embodiments are therefore merely to be seen as a descriptive disclosure which is in no way limiting.

The complete disclosure of all applications, patents and publications given above and below are incorporated into this application by reference.

The examples below serve to illustrate the invention in more detail. They are not, however, suitable for limiting the actual subject-matter of the invention to the examples given.

EXAMPLE 1

The following components are used to prepare a sunscreen cream (O/W) according to the invention.

|   |   |   | % by wt |
|---|---|---|---|
| A | Eusolex ® 9020 (Art. No. 105844) (Butylmethoxydibenzoylmethane) | (1) | 1.00 |
|   | Eusolex ® T-2000 (Art. No. 105373) | (1) | 5.00 |
|   | Arlatone 983 S | (2) | 1.50 |
|   | Arlatone 985 | (2) | 2.20 |
|   | Brij 76 | (2) | 1.50 |
|   | Miglyol 812 neutral oil | (3) | 10.00 |
| B | Sorbitol F liquid (Art. No. 102993) | (1) | 2.50 |
|   | 1,2-Propanediol (Art. No. 107478) | (1) | 2.50 |
|   | Preservatives | (1) | q.s. |
|   | Demin. water |   | ad100.00 |
| C | Carbomer 934 | (4) | 0.50 |
| D | Tris (hydroxymethyl) aminomethane (Art. No. 108386) | (1) | 0.36 |
|   | Demin. water |   | 9.64 |

Preparation:

Phase B is mixed, Carbomer 934 is added, and the mixture is left to swell until it is homogeneous. The premixed phase D is then added and the mixture is 10 homogenized. It is then heated to 800C. Phase A is combined and heated to 750° C. With slow stirring, phase A is stirred into the phase prepared previously from B–D.

Preservatives:

0.05% of propyl 4-hydroxybenzoate (Art. No. 107427)
0.15% of methyl 4-hydroxybenzoate (Art. No. 106757)

Sources of supply:

Merck KGaA, Darmstadt
ICI, Essen

Hüls Troisdorf AG, Witten

Goodrich, Neuss

EXAMPLE 2

The following components are used to prepare a sunscreen cream (O/W) according to the invention from two separate formulations.

Formulation I

|   |   |   | % by wt |
|---|---|---|---|
| A | Eusolex ® T-2000 (Art. No. 105373) | (1) | 5.00 |
|   | Arlatone 983 S | (2) | 1.50 |
|   | Arlatone 985 | (2) | 2.20 |
|   | Brij 76 | (2) | 1.50 |
|   | Miglyol 812 neutral oil | (3) | 10.00 |
| B | Sorbitol F liquid (Art. No. 102993) | (1) | 2.50 |
|   | 1,2-Propanediol (Art. No. 107478) | (1) | 2.50 |
|   | Preservatives | (1) | q.s. |
|   | Demin. water |   | ad 100.00 |
| C | Carbomer 934 | (4) | 0.50 |
| D | Tris (hydroxymethyl) aminomethane (Art. No. 108386) | (1) | 0.36 |
|   | Demin. water |   | 9.64 |

Preparation:

Phase B is mixed, Carbomer 934 is added, and the mixture is left to swell until it is homogeneous. The premixed phase D is then added and the mixture is homogenized. It is then heated to 80° C. Phase A is combined and heated to 75° C. With slow stirring, phase A is stirred into the phase prepared previously from B–D.

Preservatives:

0.05% of propyl 4-hydroxybenzoate (Art. No. 107427)

0.15% of methyl 4-hydroxybenzoate (Art. No. 106757)

Formulation II

|   |   |   | % by wt |
|---|---|---|---|
| A | Eusolex ® 9020 (Art. No. 105844) | (1) | 5.00 |
|   | Arlatone 983 S | (2) | 1.50 |
|   | Arlatone 985 | (2) | 2.20 |
|   | Brij 76 | (2) | 1.50 |
|   | Miglyol 812 neutral oil | (3) | 10.00 |
| B | Sorbitol F liquid (Art. No. 102993) | (1) | 2.50 |
|   | 1,2-Propanediol (Art. No. 107478) | (1) | 2.50 |
|   | Preservatives | (1) | q.s. |
|   | Demin. Water |   | ad 100.00 |
| C | Carbomer 934 | (4) | 0.50 |
| D | Tris (hydroxymethyl) aminomethane (Art. No. 108386) | (1) | 0.36 |
|   | Demin. water |   | 9.64 |

Preparation:

Phase B is mixed, Carbomer 934 is added, and the mixture is left to swell until it is homogeneous. The premixed phase D is then added and the mixture is homogenized. It is then heated to 80° C. Phase A is combined and heated to 75° C. With slow stirring, phase A is stirred into the phase prepared previously from B–D.

Preservatives:

0.05% of propyl 4-hydroxybenzoate (Art. No. 107427)

0.15% of methyl 4-hydroxybenzoate (Art. No. 106757)

Sources of supply:

Merck KGaA, Darmstadt

ICI, Essen

Hüls Troisdorf AG, Witten

Goodrich, Neuss

The two formulations are put into separate containers. For application, formulation I is firstly applied to the skin, followed by formulation II.

What is claimed is:

1. A process of improving the photostability of butylmethoxydibenzoyhmethane in a cosmetic composition comprising adding insoluble inorganic particles which are titanium dioxide particles doped with cerium or iron ions to said cosmetic composition.

2. A process according to claim 1, wherein the content of butyhnethoxydibenzoylmethane in the cosmetic composition is from 0.5 to 3% by weight.

3. A process according to claim 1, wherein the content of inorganic particles in the cosmetic composition is 0.5 to 10% by weight.

4. A process according to claim 1, wherein said cosmetic composition is in the form of an oily, oily-aqueous, aqueous-alcoholic or oily-alcoholic lotion, an emulsion, an oily-alcoholic, oily-aqueous, or aqueous-alcoholic gel, a solid stick, a powder, a spray or an aerosol.

5. A process according to claim 1, wherein the cosmetic composition further comprises a thickener, emollient, moisturizer, surfactant, preservative, antifoam, perfume, wax, lanolin, propellant, dye, pigment, and/or a solubilizing agent.

6. A process according to claim 1, wherein the insoluble inorganic particles have a particle size of 10 nm to 100 μm.

7. A process according to claim 1, wherein the insoluble inorganic particles are titanium dioxide microrutile doped with cerium or iron ions having a particle size of up to 10 μm.

8. A process according to claim 1, wherein the content of inorganic particles in the cosmetic composition is 0.1 to 30% by weight.

9. A process according to claim 1, wherein the content of butylmethoxydibenzoylmethane in the cosmetic composition is 0.1 to 10% by weight.

10. A process according to claim 1, wherein the cosmetic composition consists of two separate subcompositions, one subcomposition comprises butylmethoxydibenzoylmethane, and the second subcomposition comprises the inorganic particles.

\* \* \* \* \*

UNITED STATES PATENT AND TRADEMARK OFFICE
CERTIFICATE OF CORRECTION

PATENT NO. : 6,436,374 B1
DATED : August 20, 2002
INVENTOR(S) : Kurz et al.

It is certified that error appears in the above-identified patent and that said Letters Patent is hereby corrected as shown below:

<u>Column 6,</u>
Line 19, "butyhnethoxydibenzoylmethane" should be -- butylmethoxydibenzoylmethane --.

Signed and Sealed this

Twenty-second Day of March, 2005

JON W. DUDAS
*Director of the United States Patent and Trademark Office*